United States Patent [19]
Houghton et al.

[11] Patent Number: 5,989,905
[45] Date of Patent: Nov. 23, 1999

[54] HCV NS3 PROTEIN FRAGMENTS HAVING HELICASE ACTIVITY AND IMPROVED SOLUBILITY

[75] Inventors: Michael Houghton, Danville; Qui-Lim Choo, El Cerrito; Jang Han, Lafayette, all of Calif.; Joonho Choe, Taejon, Rep. of Korea

[73] Assignee: Chiron Corporation, Emeryville, Calif.

[21] Appl. No.: 08/833,678

[22] Filed: Apr. 8, 1997

Related U.S. Application Data

[62] Division of application No. 08/529,169, Sep. 15, 1995.

[51] Int. Cl.[6] .............................. C12N 15/00; C07H 21/04
[52] U.S. Cl. .................... 435/320.1; 536/23.2; 536/23.4; 536/23.72
[58] Field of Search ................................ 435/69.7, 320.1, 435/183; 536/23.2, 23.4, 23.72

[56] References Cited

U.S. PATENT DOCUMENTS

| | | |
|---|---|---|
| 4,870,008 | 9/1989 | Brake ....................................... 435/69.4 |
| 5,350,671 | 9/1994 | Houghton et al. ........................... 435/5 |
| 5,371,017 | 12/1994 | Houghton et al. .................... 435/320.1 |

FOREIGN PATENT DOCUMENTS

| | | |
|---|---|---|
| 0 116 201 | 8/1984 | European Pat. Off. . |
| 0 120 551 | 10/1984 | European Pat. Off. . |
| 0 164 556 | 12/1985 | European Pat. Off. . |
| 450 931 A1 | 10/1991 | European Pat. Off. . |
| 0 318 216-B1 | 12/1993 | European Pat. Off. . |
| 6-319583 | 11/1994 | Japan . |

OTHER PUBLICATIONS

Kim, et al., *Biochemical & Biophysical Research Comm.*, (1995) 215(1):160–166.
Patent Abstracts of Japan, vol. 095, No. 002, Mar. 31, 1995 & JP 06 319583 A (Souyaku Gijutsu Kenkyusho:KK), Nov. 22, 1994.
Faila et al., *J. Virol.* 68:3753–3760 (1994).
Choo et al., *PNAS*, 88:2451–2455 (1991).
Gorbalenya et al., *Nucleic Acids Res.*, 17:4713–4729 (1989).
Suzich et al., *J Virol*, 67–6152–6158 (1993).
Gwack et al., *Mol. Cells.* 5(2) : 171–175 (1995).
Warrener et al., "Pestivirus NS3 (p80) Protein Possesses RNA Helicase Activity," *J. Virol.* 69:1720–1726, (1995).
Lee et al., *J. Biol.* 267:4398–4407 (1992).
Clewell et al, *Proc Nat Acad Sci USA* (1969) 62:1159.
Clewell, *J Bacteriol* (1972) 110:667.

*Primary Examiner*—Ponnathapura Achutamurthy
*Assistant Examiner*—Elizabeth Slobodyansky
*Attorney, Agent, or Firm*—Alisa A. Harbin; Woodcock Washburn Kurtz Mackiewicz & Norris; Robert P Blackburn

[57] ABSTRACT

The Hepatitis C Virus (HCV) NS3 protein contains amino acid motifs of a serine proteinase, a nucleotide triphosphatase (NTPase), and an RNA helicase. A carboxy fragment of the HCV NS3 protein was purified and possessed RNA helicase activity. Detections from the amino terminus resulted in the protein becoming soluble. Deletions from the carboxy terminus do not result in a loss of helicase activity until at least 50 amino acids are deleted. The helicase activity requires ATP and divalent cations such as $Mg^{2+}$ and $Mn^{2+}$. The helicase activity was blocked by monoclonal antibody specific to the HCV NS3 protein.

15 Claims, 4 Drawing Sheets

APITAYAQQTRGLLGCIITSLTGR
DKNQVEGEVQIVSTAAQTFLATCINGVCWTVYHGAGTRTIASPKGPVIQM-1100
                  S       T
YTNVDQDLVGWPAPQGSRSLTPCTCGSSDLYLVTRHADVIPVRRGDSRG
SLLSPRPISYLKGSSGGPLLCPAGHAVGIFRAAVCTRGVAKAVDFIPVEN-1200
LETTMRSPVFTDNSSPPVVPQSFQVAHLHAPTGSGKSTKVPAAYAAQGYK
                         L
VLVLNPSVAATLGFGAYMSKAHGIDPNIRTGVRTITTGSPITYSTYGKFL-1300
ADGGCSGGAYDIIICDECHSTDATSILGIGTVLDQAETAGARLVVLATAT
PPGSVTVPHPNIEEVALSTTGEIPFYGKAIPLEVIKGGRHLIFCHSKKKC-1400
DELAAKLVALGINAVAYYRGLDVSVIPTSGDVVVVATDALMTGYTGDFDS
       Y         (S)
VIDCNTCVTQTVDFSLDPTFTIETITLPQDAVSRTQRRGRTGRGKPGIYR-1500
FVAPGERPSGMFDSSVLCECYDAGCAWYELTPAETTVRLRAYMNTPGLPV
CQDHLEFWEGVFTGLTHIDAHFLSQTKQSGENLPYLVAYQATVCARAQAP-1600
PPSWDQMWKCLIRLKPTLHGPTPLLYRLGAVQNEITLTHPVTKYIMTCMS
ADLEVVT

*FIG. 1*

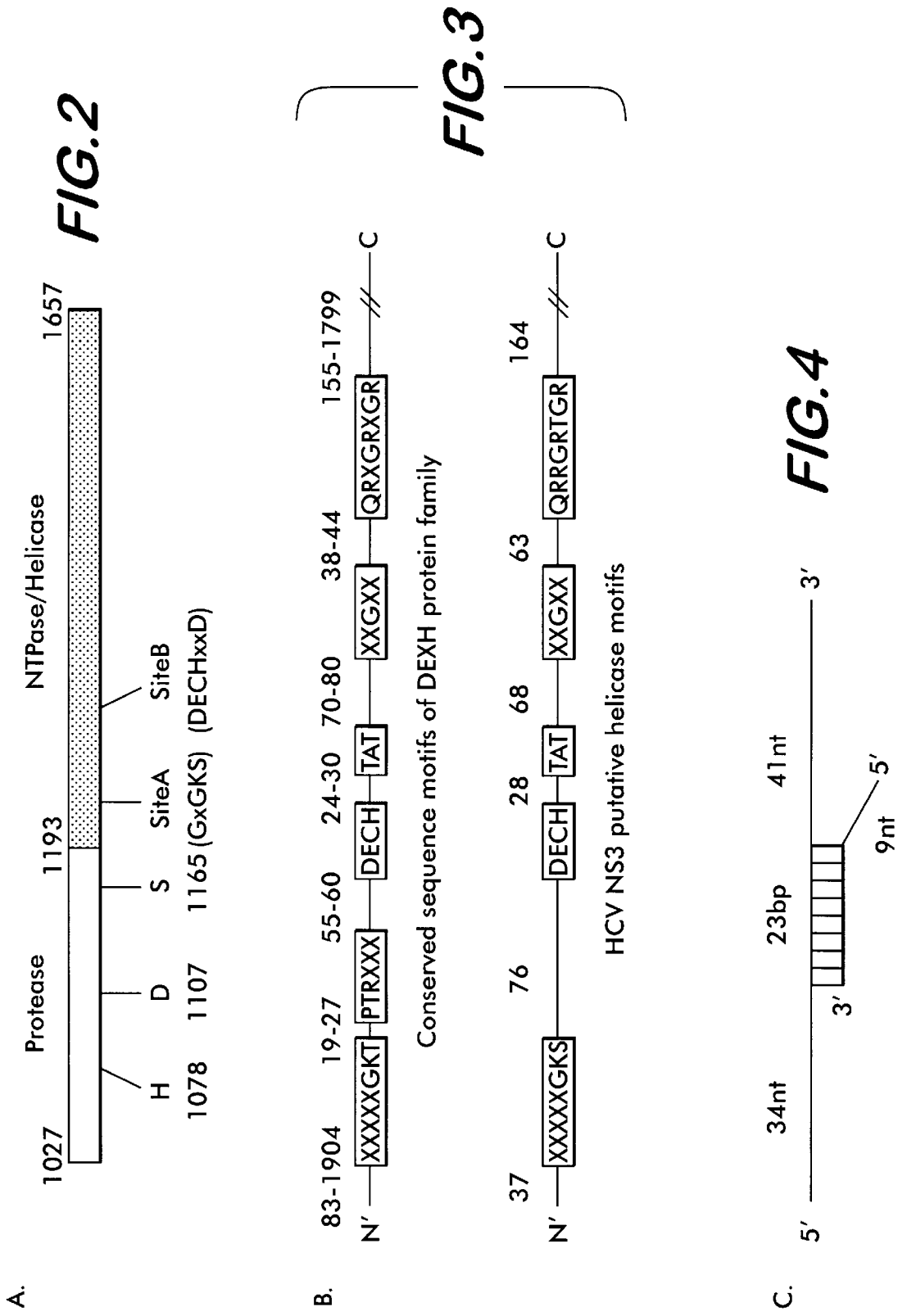

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 631 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ala Pro Ile Thr Ala Tyr Ala Gln Gln Thr Arg Gly Leu Leu Gly Cys
 1               5                  10                  15

Ile Ile Thr Ser Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
            35                  40                  45

Asn Gly Val Cys Trp Thr Val Tyr His Gly Ala Gly Thr Arg Thr Ile
50                  55                  60
```

```
Ala Ser Pro Lys Gly Pro Val Ile Gln Met Tyr Thr Asn Val Asp Gln
 65                  70                  75                  80

Asp Leu Val Gly Trp Pro Ala Pro Gln Gly Ser Arg Ser Leu Thr Pro
                 85                  90                  95

Cys Thr Cys Gly Ser Ser Asp Leu Tyr Leu Val Thr Arg His Ala Asp
                100                 105                 110

Val Ile Pro Val Arg Arg Gly Asp Ser Arg Gly Ser Leu Leu Ser
            115                 120                 125

Pro Arg Pro Ile Ser Tyr Leu Lys Gly Ser Ser Gly Pro Leu Leu
    130                 135                 140

Cys Pro Ala Gly His Ala Val Gly Ile Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Val
            180                 185                 190

Val Pro Gln Ser Phe Gln Val Ala His Leu His Ala Pro Thr Gly Ser
    195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ala Thr Ser Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Thr Thr Gly Glu Ile Pro Phe Tyr Gly Lys
            340                 345                 350

Ala Ile Pro Leu Glu Val Ile Lys Gly Gly Arg His Leu Ile Phe Cys
        355                 360                 365

His Ser Lys Lys Lys Cys Asp Glu Leu Ala Ala Lys Leu Val Ala Leu
    370                 375                 380

Gly Ile Asn Ala Val Ala Tyr Tyr Arg Gly Leu Asp Val Ser Val Ile
385                 390                 395                 400

Pro Thr Ser Gly Asp Val Val Val Ala Thr Asp Ala Leu Met Thr
                405                 410                 415

Gly Tyr Thr Gly Asp Phe Asp Ser Val Ile Asp Cys Asn Thr Cys Val
                420                 425                 430

Thr Gln Thr Val Asp Phe Ser Leu Asp Pro Thr Phe Thr Ile Glu Thr
        435                 440                 445

Ile Thr Leu Pro Gln Asp Ala Val Ser Arg Thr Gln Arg Arg Gly Arg
    450                 455                 460

Thr Gly Arg Gly Lys Pro Gly Ile Tyr Arg Phe Val Ala Pro Gly Glu
465                 470                 475                 480

Arg Pro Ser Gly Met Phe Asp Ser Ser Val Leu Cys Glu Cys Tyr Asp
```

```
                     485                 490                 495
Ala Gly Cys Ala Trp Tyr Glu Leu Thr Pro Ala Glu Thr Thr Val Arg
            500                 505                 510

Leu Arg Ala Tyr Met Asn Thr Pro Gly Leu Pro Val Cys Gln Asp His
            515                 520                 525

Leu Glu Phe Trp Glu Gly Val Phe Thr Gly Leu Thr His Ile Asp Ala
            530                 535                 540

His Phe Leu Ser Gln Thr Lys Gln Ser Gly Glu Asn Leu Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
            595                 600                 605

Ile Thr Leu Thr His Pro Val Thr Lys Tyr Ile Met Thr Cys Met Ser
            610                 615                 620

Ala Asp Leu Glu Val Val Thr
625                 630

(2) INFORMATION FOR SEQ ID NO:2:

(i) SEQUENCE CHARACTERISTICS:
        (A) LENGTH: 465 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Val Asp Phe Ile Pro Val Glu Asn Leu Glu Thr Thr Met Arg Ser Pro
1               5                   10                  15

Val Phe Thr Asp Asn Ser Ser Pro Pro Val Val Pro Gln Ser Phe Gln
            20                  25                  30

Val Ala His Leu His Ala Pro Thr Gly Ser Gly Lys Ser Thr Lys Val
            35                  40                  45

Pro Ala Ala Tyr Ala Ala Gln Gly Tyr Lys Val Leu Val Leu Asn Pro
            50                  55                  60

Ser Val Ala Ala Thr Leu Gly Phe Gly Ala Tyr Met Ser Lys Ala His
65                  70                  75                  80

Gly Ile Asp Pro Asn Ile Arg Thr Gly Val Arg Thr Ile Thr Thr Gly
            85                  90                  95

Ser Pro Ile Thr Tyr Ser Thr Tyr Gly Lys Phe Leu Ala Asp Gly Gly
            100                 105                 110

Cys Ser Gly Gly Ala Tyr Asp Ile Ile Ile Cys Asp Glu Cys His Ser
            115                 120                 125

Thr Asp Ala Thr Ser Ile Leu Gly Ile Gly Thr Val Leu Asp Gln Ala
            130                 135                 140

Glu Thr Ala Gly Ala Arg Leu Val Val Leu Ala Thr Ala Thr Pro Pro
145                 150                 155                 160

Gly Ser Val Thr Val Pro His Pro Asn Ile Glu Glu Val Ala Leu Ser
            165                 170                 175

Thr Thr Gly Glu Ile Pro Phe Tyr Gly Lys Ala Ile Pro Leu Glu Val
            180                 185                 190

Ile Lys Gly Gly Arg His Leu Ile Phe Cys His Ser Lys Lys Lys Cys
            195                 200                 205
```

```
Asp Glu Leu Ala Ala Lys Leu Val Ala Leu Gly Ile Asn Ala Val Ala
    210                 215                 220

Tyr Tyr Arg Gly Leu Asp Val Ser Val Ile Pro Thr Ser Gly Asp Val
225                 230                 235                 240

Val Val Val Ala Thr Asp Ala Leu Met Thr Gly Tyr Thr Gly Asp Phe
                245                 250                 255

Asp Ser Val Ile Asp Cys Asn Thr Cys Val Thr Gln Thr Val Asp Phe
                260                 265                 270

Ser Leu Asp Pro Thr Phe Thr Ile Glu Thr Ile Thr Leu Pro Gln Asp
            275                 280                 285

Ala Val Ser Arg Thr Gln Arg Arg Gly Arg Thr Gly Arg Gly Lys Pro
        290                 295                 300

Gly Ile Tyr Arg Phe Val Ala Pro Gly Glu Arg Pro Ser Gly Met Phe
305                 310                 315                 320

Asp Ser Ser Val Leu Cys Glu Cys Tyr Asp Ala Gly Cys Ala Trp Tyr
                325                 330                 335

Glu Leu Thr Pro Ala Glu Thr Thr Val Arg Leu Arg Ala Tyr Met Asn
            340                 345                 350

Thr Pro Gly Leu Pro Val Cys Gln Asp His Leu Glu Phe Trp Glu Gly
        355                 360                 365

Val Phe Thr Gly Leu Thr His Ile Asp Ala His Phe Leu Ser Gln Thr
    370                 375                 380

Lys Gln Ser Gly Glu Asn Leu Pro Tyr Leu Val Ala Tyr Gln Ala Thr
385                 390                 395                 400

Val Cys Ala Arg Ala Gln Ala Pro Pro Pro Ser Trp Asp Gln Met Trp
                405                 410                 415

Lys Cys Leu Ile Arg Leu Lys Pro Thr Leu His Gly Pro Thr Pro Leu
            420                 425                 430

Leu Tyr Arg Leu Gly Ala Val Gln Asn Glu Ile Thr Leu Thr His Pro
        435                 440                 445

Val Thr Lys Tyr Ile Met Thr Cys Met Ser Ala Asp Leu Glu Val Val
    450                 455                 460

Thr
465

(2) INFORMATION FOR SEQ ID NO:3:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Gln Ile Phe Val Lys Thr Leu Thr Gly Lys Thr Ile Thr Leu Glu Val
1               5                   10                  15

Glu Ser Ser Asp Thr Ile Asp Asn Val Lys Ser Lys Ile Gln Asp Lys
                20                  25                  30

Glu Gly Ile Pro Pro Asp Gln Gln Arg Leu Ile Phe Ala Gly Lys Gln
            35                  40                  45

Leu Glu Asp Gly Arg Thr Leu Ser Asp Tyr Asn Ile Gln Lys Glu Ser
    50                  55                  60

Thr Leu His Leu Val Leu Arg Leu Arg Gly Gly
65                  70                  75
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:4:

GGGGATCCGG TGGACTTTAT CCCT                                      24

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:5:

GGAAGCTTGC TGACGACCTC G                                        21

(2) INFORMATION FOR SEQ ID NO:6:

(i) SEQUENCE CHARACTERISTICS:
        (A) LENGTH: 3011 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Duplication
        (B) LOCATION: 9
        (D) OTHER INFORMATION: /note= "There exists a
            heterogeneity at this position - Xaa = Lys or Arg"

(ix) FEATURE:
        (A) NAME/KEY: Duplication
        (B) LOCATION: 11
        (D) OTHER INFORMATION: /note= "There exists a
            heterogeneity at this position - Xaa = Asn or Thr"

(ix) FEATURE:
        (A) NAME/KEY: Duplication
        (B) LOCATION: 176
        (D) OTHER INFORMATION: /note= "There exists a
            heterogeneity at this position - Xaa = Ile or Thr"

(ix) FEATURE:
        (A) NAME/KEY: Duplication
        (B) LOCATION: 334
        (D) OTHER INFORMATION: /note= "There exists a
            heterogeneity at this position - Xaa = Met or Val"

(ix) FEATURE:
        (A) NAME/KEY: Duplication
        (B) LOCATION: 603
        (D) OTHER INFORMATION: /note= "There exists a
            heterogeneity at this position - Xaa = Leu or Ile"

(ix) FEATURE:
        (A) NAME/KEY: Duplication
        (B) LOCATION: 848
        (D) OTHER INFORMATION: /note= "There exists a
            heterogeneity at this position - Xaa = Tyr or Asn"

(ix) FEATURE:
        (A) NAME/KEY: Duplication
        (B) LOCATION: 1114

(D) OTHER INFORMATION: /note= "There exists a
                        heterogeneity at this position - Xaa = Pro or Ser"

(ix) FEATURE:
                    (A) NAME/KEY: Duplication
                    (B) LOCATION: 1117
                    (D) OTHER INFORMATION: /note= "There exists a
                        heterogeneity at this position - Xaa = Ser or Thr"

(ix) FEATURE:
                    (A) NAME/KEY: Duplication
                    (B) LOCATION: 1276
                    (D) OTHER INFORMATION: /note= "There exists a
                        heterogeneity at this position - Xaa = Pro or Leu"

(ix) FEATURE:
                    (A) NAME/KEY: Duplication
                    (B) LOCATION: 1454
                    (D) OTHER INFORMATION: /note= "There exists a
                        heterogeneity at this position - Xaa = Cys or Tyr"

(ix) FEATURE:
                    (A) NAME/KEY: Duplication
                    (B) LOCATION: 1471
                    (D) OTHER INFORMATION: /note= "There exists a
                        heterogeneity at this position - Xaa = Thr or  Ser"

(ix) FEATURE:
                    (A) NAME/KEY: Duplication
                    (B) LOCATION: 1877
                    (D) OTHER INFORMATION: /note= "There exists a
                        heterogeneity at this position - Xaa = Glu or Gly"

(ix) FEATURE:
                    (A) NAME/KEY: Duplication
                    (B) LOCATION: 1948
                    (D) OTHER INFORMATION: /note= "There exists a
                        heterogeneity at this position - Xaa = Leu or His"

(ix) FEATURE:
                    (A) NAME/KEY: Duplication
                    (B) LOCATION: 1949
                    (D) OTHER INFORMATION: /note= "There exists a
                        heterogeneity at this position - Xaa = Ser or Cys"

(ix) FEATURE:
                    (A) NAME/KEY: Duplication
                    (B) LOCATION: 2021
                    (D) OTHER INFORMATION: /note= "There exists a
                        heterogeneity at this position - Xaa = Gly or Val"

(ix) FEATURE:
                    (A) NAME/KEY: Duplication
                    (B) LOCATION: 2349
                    (D) OTHER INFORMATION: /note= "There exists a
                        heterogeneity at this position - Xaa = Thr or Ser"

(ix) FEATURE:
                    (A) NAME/KEY: Duplication
                    (B) LOCATION: 2385
                    (D) OTHER INFORMATION: /note= "There exists a
                        heterogeneity at this position - Xaa = Tyr or  Phe"

(ix) FEATURE:
                    (A) NAME/KEY: Duplication
                    (B) LOCATION: 2386
                    (D) OTHER INFORMATION: /note= "There exists a
                        heterogeneity at this position - Xaa = Ser or  Ala"

(ix) FEATURE:
                    (A) NAME/KEY: Duplication
                    (B) LOCATION: 2502
                    (D) OTHER INFORMATION: /note= "There exists a
                        heterogeneity at this position - Xaa = Leu or Phe"

(ix) FEATURE:
                    (A) NAME/KEY: Duplication
                    (B) LOCATION: 2690
                    (D) OTHER INFORMATION: /note= "There exists a
                        heterogeneity at this position - Xaa = Arg  or  Gly"

```
     (ix) FEATURE:
          (A) NAME/KEY: Duplication
          (B) LOCATION: 2921
          (D) OTHER INFORMATION: /note= "There exists a
              heterogeneity at this position - Xaa = Arg or  Gly"

(ix) FEATURE:
          (A) NAME/KEY: Duplication
          (B) LOCATION: 2996
          (D) OTHER INFORMATION: /note= "There exists a
              heterogeneity at this position - Xaa = Leu or  Pro"

(xi) SEQUENCE DESCRIPTION: SEQ ID NO:6:

Met Ser Thr Asn Pro Lys Pro Gln Xaa Lys Xaa Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                      60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
            130                 135                 140

Gly Ser Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Xaa
                165                 170                 175

Phe Leu Leu Ala Leu Leu Ser Cys Leu Thr Val Pro Ala Ser Ala Tyr
                180                 185                 190

Gln Val Arg Asn Ser Thr Gly Leu Tyr His Val Thr Asn Asp Cys Pro
                195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Gly Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Xaa Ala Gln
                325                 330                 335

Leu Leu Arg Ile Pro Gln Ala Ile Leu Asp Met Ile Ala Gly Ala His
                340                 345                 350
```

-continued

```
Trp Gly Val Leu Ala Gly Ile Ala Tyr Phe Ser Met Val Gly Asn Trp
        355                 360                 365

Ala Lys Val Leu Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Xaa Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
```

-continued

```
                  770                 775                 780
Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Leu Trp Trp Leu Gln Xaa
                835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Phe Cys Ala Leu Ala Arg Lys Met
                915                 920                 925

Ile Gly Gly His Tyr Val Gln Met Val Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Arg
                995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
                1060                1065                1070

Cys Ile Asn Gly Val Cys Trp Thr Val Tyr His Gly Ala Gly Thr Arg
                1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Xaa Gln Gly Xaa Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Ile Ser Tyr Leu Lys Gly Ser Ser Gly Gly Pro
                1155                1160                1165

Leu Leu Cys Pro Ala Gly His Ala Val Gly Ile Phe Arg Ala Ala Val
                1170                1175                1180

Cys Thr Arg Gly Val Ala Lys Ala Val Asp Phe Ile Pro Val Glu Asn
1185                1190                1195                1200
```

```
Leu Glu Thr Thr Met Arg Ser Pro Val Phe Thr Asp Asn Ser Ser Pro
            1205                1210                1215
Pro Val Val Pro Gln Ser Phe Gln Val Ala His Leu His Ala Pro Thr
        1220                1225                1230
Gly Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Gly Phe
1250                1255                1260
Gly Ala Tyr Met Ser Lys Ala His Gly Ile Asp Xaa Asn Ile Arg Thr
1265                1270                1275                1280
Gly Val Arg Thr Ile Thr Thr Gly Ser Pro Ile Thr Tyr Ser Thr Tyr
            1285                1290                1295
Gly Lys Phe Leu Ala Asp Gly Gly Cys Ser Gly Gly Ala Tyr Asp Ile
        1300                1305                1310
Ile Ile Cys Asp Glu Cys His Ser Thr Asp Ala Thr Ser Ile Leu Gly
    1315                1320                1325
Ile Gly Thr Val Leu Asp Gln Ala Glu Thr Ala Gly Ala Arg Leu Val
1330                1335                1340
Val Leu Ala Thr Ala Thr Pro Pro Gly Ser Val Thr Val Pro His Pro
1345                1350                1355                1360
Asn Ile Glu Glu Val Ala Leu Ser Thr Thr Gly Glu Ile Pro Phe Tyr
            1365                1370                1375
Gly Lys Ala Ile Pro Leu Glu Val Ile Lys Gly Gly Arg His Leu Ile
        1380                1385                1390
Phe Cys His Ser Lys Lys Lys Cys Asp Glu Leu Ala Ala Lys Leu Val
    1395                1400                1405
Ala Leu Gly Ile Asn Ala Val Ala Tyr Tyr Arg Gly Leu Asp Val Ser
    1410                1415                1420
Val Ile Pro Thr Ser Gly Asp Val Val Val Ala Thr Asp Ala Leu
1425                1430                1435                1440
Met Thr Gly Tyr Thr Gly Asp Phe Asp Ser Val Ile Asp Xaa Asn Thr
            1445                1450                1455
Cys Val Thr Gln Thr Val Asp Phe Ser Leu Asp Pro Thr Phe Xaa Ile
        1460                1465                1470
Glu Thr Ile Thr Leu Pro Gln Asp Ala Val Ser Arg Thr Gln Arg Arg
    1475                1480                1485
Gly Arg Thr Gly Arg Gly Lys Pro Gly Ile Asn Arg Phe Val Ala Pro
    1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Thr
            1525                1530                1535
Val Arg Leu Arg Ala Tyr Met Asn Thr Pro Gly Leu Pro Val Cys Gln
        1540                1545                1550
Asp His Leu Glu Phe Trp Glu Gly Val Phe Thr Gly Leu Thr His Ile
    1555                1560                1565
Asp Ala His Phe Leu Ser Gln Thr Lys Gln Ser Gly Glu Asn Leu Pro
    1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
            1605                1610                1615
Thr Leu His Gly Pro Thr Pro Leu Leu Tyr Arg Leu Gly Ala Val Gln
        1620                1625                1630
```

```
Asn Glu Ile Thr Leu Thr His Pro Val Thr Lys Tyr Ile Met Thr Cys
    1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
        1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
        1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Xaa Asp Leu Val Asn Leu Leu Pro Ala Ile Leu Ser
            1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Xaa Xaa Ser Leu Thr
            1940                1945                1950

Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
        1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
                2005                2010                2015

Gly Val Trp Arg Xaa Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Arg Thr Cys Arg Asn Met Trp Ser Gly Thr Phe Pro Ile Asn Ala
```

```
                2050              2055              2060
Tyr Thr Thr Gly Pro Cys Thr Pro Leu Pro Ala Pro Asn Tyr Thr Phe
2065            2070              2075              2080

Ala Leu Trp Arg Val Ser Ala Glu Glu Tyr Val Glu Ile Arg Gln Val
            2085              2090              2095

Gly Asp Phe His Tyr Val Thr Gly Met Thr Thr Asp Asn Leu Lys Cys
        2100              2105              2110

Pro Cys Gln Val Pro Ser Pro Glu Phe Phe Thr Glu Leu Asp Gly Val
        2115              2120              2125

Arg Leu His Arg Phe Ala Pro Pro Cys Lys Pro Leu Leu Arg Glu Glu
    2130              2135              2140

Val Ser Phe Arg Val Gly Leu His Glu Tyr Pro Val Gly Ser Gln Leu
2145              2150              2155              2160

Pro Cys Glu Pro Glu Pro Asp Val Ala Val Leu Thr Ser Met Leu Thr
                2165              2170              2175

Asp Pro Ser His Ile Thr Ala Glu Ala Ala Gly Arg Arg Leu Ala Arg
            2180              2185              2190

Gly Ser Pro Pro Ser Val Ala Ser Ser Ser Ala Ser Gln Leu Ser Ala
        2195              2200              2205

Pro Ser Leu Lys Ala Thr Cys Thr Ala Asn His Asp Ser Pro Asp Ala
        2210              2215              2220

Glu Leu Ile Glu Ala Asn Leu Leu Trp Arg Gln Glu Met Gly Gly Asn
2225              2230              2235              2240

Ile Thr Arg Val Glu Ser Glu Asn Lys Val Val Ile Leu Asp Ser Phe
                2245              2250              2255

Asp Pro Leu Val Ala Glu Glu Asp Glu Arg Glu Ile Ser Val Pro Ala
            2260              2265              2270

Glu Ile Leu Arg Lys Ser Arg Arg Phe Ala Gln Ala Leu Pro Val Trp
        2275              2280              2285

Ala Arg Pro Asp Tyr Asn Pro Pro Leu Val Glu Thr Trp Lys Lys Pro
        2290              2295              2300

Asp Tyr Glu Pro Pro Val Val His Gly Cys Pro Leu Pro Pro Pro Lys
2305              2310              2315              2320

Ser Pro Pro Val Pro Pro Pro Arg Lys Lys Arg Thr Val Val Leu Thr
                2325              2330              2335

Glu Ser Thr Leu Ser Thr Ala Leu Ala Glu Leu Ala Xaa Arg Ser Phe
            2340              2345              2350

Gly Ser Ser Ser Thr Ser Gly Ile Thr Gly Asp Asn Thr Thr Thr Ser
        2355              2360              2365

Ser Glu Pro Ala Pro Ser Gly Cys Pro Pro Asp Ser Asp Ala Glu Ser
        2370              2375              2380

Xaa Xaa Ser Met Pro Pro Leu Glu Gly Glu Pro Gly Asp Pro Asp Leu
2385              2390              2395              2400

Ser Asp Gly Ser Trp Ser Thr Val Ser Ser Glu Ala Asn Ala Glu Asp
            2405              2410              2415

Val Val Cys Cys Ser Met Ser Tyr Ser Trp Thr Gly Ala Leu Val Thr
            2420              2425              2430

Pro Cys Ala Ala Glu Glu Gln Lys Leu Pro Ile Asn Ala Leu Ser Asn
        2435              2440              2445

Ser Leu Leu Arg His His Asn Leu Val Tyr Ser Thr Thr Ser Arg Ser
    2450              2455              2460

Ala Cys Gln Arg Gln Lys Lys Val Thr Phe Asp Arg Leu Gln Val Leu
2465              2470              2475              2480
```

-continued

```
Asp Ser His Tyr Gln Asp Val Leu Lys Glu Val Lys Ala Ala Ser
                2485                2490                2495

Lys Val Lys Ala Asn Xaa Leu Ser Val Glu Glu Ala Cys Ser Leu Thr
                2500                2505                2510

Pro Pro His Ser Ala Lys Ser Lys Phe Gly Tyr Gly Ala Lys Asp Val
                2515                2520                2525

Arg Cys His Ala Arg Lys Ala Val Thr His Ile Asn Ser Val Trp Lys
                2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
                2580                2585                2590

Met Ala Leu Tyr Asp Val Val Thr Lys Leu Pro Leu Ala Val Met Gly
                2595                2600                2605

Ser Ser Tyr Gly Phe Gln Tyr Ser Pro Gly Gln Arg Val Glu Phe Leu
                2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
                2660                2665                2670

Ile Lys Ser Leu Thr Glu Arg Leu Tyr Val Gly Gly Pro Leu Thr Asn
                2675                2680                2685

Ser Xaa Gly Glu Asn Cys Gly Tyr Arg Arg Cys Arg Ala Ser Gly Val
                2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
                2740                2745                2750

Ala Ala Ser Leu Arg Ala Phe Thr Glu Ala Met Thr Arg Tyr Ser Ala
                2755                2760                2765

Pro Pro Gly Asp Pro Pro Gln Pro Glu Tyr Asp Leu Glu Leu Ile Thr
                2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
                2820                2825                2830

Ile Met Phe Ala Pro Thr Leu Trp Ala Arg Met Ile Leu Met Thr His
                2835                2840                2845

Phe Phe Ser Val Leu Ile Ala Arg Asp Gln Leu Glu Gln Ala Leu Asp
                2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
                2900                2905                2910
```

```
Gly Val Pro Pro Leu Arg Ala Trp Xaa His Arg Ala Arg Ser Val Arg
        2915                2920                2925

Ala Arg Leu Leu Ala Arg Gly Gly Arg Ala Ala Ile Cys Gly Lys Tyr
        2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ile
                2980                2985                2990

Trp Phe Cys Xaa Leu Leu Leu Ala Ala Gly Val Gly Ile Tyr Leu Leu
        2995                3000                3005

Pro Asn Arg
    3010
```

HCV NS3 PROTEIN FRAGMENTS HAVING HELICASE ACTIVITY AND IMPROVED SOLUBILITY

CROSS-REFERENCE TO RELATED APPLICATIONS

This application is a divisional of application Ser. No. 08/529,169, filed Sep. 15, 1995.

TECHNICAL FIELD

This invention relates to the molecular biology and virology of the hepatitis C virus (HCV). More specifically, this invention relates to (1) carboxy terminus fragments of the HCV NS3 protein having helicase activity and improved solubility in extraction and assay buffers, (2) methods of expressing the novel NS3 protein fragments having helicase activity and improved solubility; (3) recombinant NS3 protein fragments having helicase activity and improved solubility; (4) NS3 protein mutant fragments; and (5) method of using the HCV NS3 protein fragments for screening helicase inhibitors as potential therapeutic agents.

BACKGROUND OF THE INVENTION

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-borne epidemic type; the blood or needle associated type; and the sporadically occurring (community acquired) type. However, the number of causative agents is unknown. Recently, however, a new viral species, hepatitis C virus (HCV) has been identified as the primary (if not only) cause of blood-associated NANBH (BB-NANBH). See for example, PCT WO89/046699; U.S. patent application Ser. No. 7/456,637, filed Dec. 21, 1989; and U.S. patent application Ser. No. 7/456,637, filed Dec. 21, 1989, incorporated herein by reference. Hepatitis C appears to be the major form of transfusion-associated hepatitis in a number of countries, including the United States and Japan. There is also evidence implicating HCV in induction of hepatocellular carcinoma. Thus, a need exists for an effective method for treating HCV infection: currently, there is none.

HCV is a positive strand RNA virus. Upon infection, its genomic RNA produces a large polyprotein that is processed by viral and cellular proteins into at least 10 different viral proteins. Like other positive strand RNA viruses, replication of the positive strand involves initial synthesis of a negative strand RNA. This negative strand RNA, which is a replication intermediate, serves as a template for the production of progeny genomic RNA. This process is believed to be carried out by two or more viral encoded enzymes, including RNA-dependent RNA polymerase and RNA helicase. RNA polymerase copies template RNA for the production of progeny RNA. This enzyme does not synthesize RNA molecules from DNA template.

The RNA helicase unwinds the secondary structure present in the single-strand RNA molecule. The helicase also unwinds the duplex RNA into single-strand forms. Genomic HCV RNA molecules contain extensive secondary structure. Replication intermediates of HCV RNA are believed to be present as duplex RNA consisting of positive and negative strand RNA molecules. The activity of RNA helicase is believed to be crucial to RNA dependent RNA polymerase which requires unwound single stranded RNA molecules as a template. Therefor, the biological activity of helicase is believed to be required for HCV replication.

NS3 proteins of the three genera of the Flaviviridae family: flavivirus, pestivirus and HCV, have been shown to have conserved sequence motifs of a serine-type proteinase and of a nucleoside triphosphatase (NTPase)/RNA helicase. One third of the N'-terminal of the HCV NS3 protein has been shown to be a trypsin like serine proteinase which cleaves the NS3-NS4A, NS4A-NS4B, NS4B-NS5A, and NS60A-NS5B junctions. Faila et al., *J. Virol.* 68:3753–3760 (1994). Two thirds of the NS3 C'-terminal fragment has been shown to encode NTPase/RNA helicase activity. Choo et al., *PNAS*, 88:2451–2455 (1991) and Gorbalenya et al., *Nucleic Acids Res.*, 17:4713–4729 (1989). Suzich et al. showed that two thirds of the carboxy terminal fragment of HCV NS3 expressed in *E. coli* had polynucleotide-stimulated NTPase activity. *J. Virol*, 67:6152–6158 (1993). Gwack et al., in "NTPase Activity of Hepatitis C Virus NS3 Protein Expressed in Insect Cells" *Mol. Cells.* 5(2): 171–175 (1995), showed two HCV NS3 proteins, p70 and p43, were expressed in a baculovirus expression system. The p70 showed a specific NTPase activity that was inhibited by NS3 monoclonal antibodies. Warrener et al., "Pestivirus NS3 (p80) Protein Possesses RNA Helicase Activity," *J. Virol.* 69:1720–1726 (1995), demonstrated that bovine viral diarrhea virus (BVDV) NS3 protein expressed in a baculovirus expression system had a RNA helicase activity. JP 0631 9583A describes the preparation of a helicase protein encoded by HCV by introducing a HCV helicase gene into the non-essential region of a baculovirus. The helicase amino acid sequence is reported as 1200 through 1500 of the HCV polyprotein. All documents mentioned above are incorporated herein in their entirety by reference.

DISCLOSURE OF THE INVENTION

We have now invented recombinant HCV NS3 protein fragments having helicase activity and improved solubility, fusion HCV NS3 protein fragments having helicase activity and improved solubility, truncated and altered HCV NS3 protein fragments having helicase activity and improved solubility, and cloning and expression vectors therefore, and methods for using these protein fragments in screening assays to assess whether a compound is capable of inhibiting RNA helicase activity and thus inhibiting HCV replication.

BRIEF DESCRIPTION OF THE DRAWINGS

FIG. 1 shows the sequence of the of the NS3 protein of HCV-1, which is approximately from amino acid 1027 to 1657 of the HCV-1 polyprotein. (SEQ ID NO: 1)

FIG. 2 is a schematic presentation of the HCV NS3 protein. The numbers indicate the amino acid positions of the HCV-1 polyprotein.

FIG. 3 shows the conserved sequence motif of DEXH box RNA helicase proteins and comparative alignment of the RNA helicase domain of the HCV NS3 protein. The numbers between boxes indicate the distance in amino acids residues.

FIG. 4 shows the structure of double strand RNA substrate for RNA helicase assay. The thick line indicates the $^{32}$P-labeled RNA strand. The thin line indicates the unlabeled RNA strand.

MODES OF CARRYING OUT THE INVENTION

A. Definitions

Figure 5:
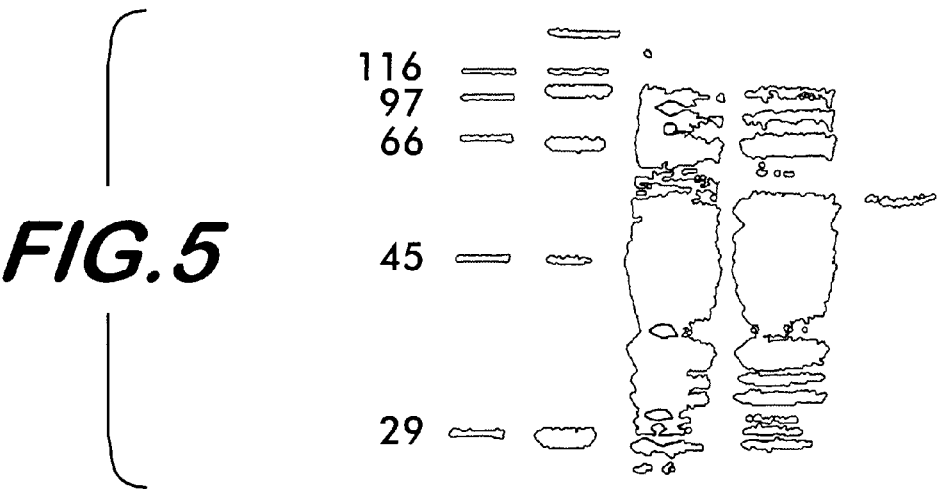
FIG. 5 shows the expression and purification of HCV NS3 from *E. Coli*. M: protein size markers, Lane 1: Total protein from uninduced cells, Lane 2: Total protein from 3 hr IPTG induced cells, Lane 3: HCV NS3:His-tag fusion protein purified by nickel binding chromatography.

The terms "Hepatitis C Virus" and "HCV" refer to the viral species that is the major etiological agent of BB-NANBH, the prototype isolate of which is identified in PCT WO89/046699; EPO publication 318,216; U.S. Ser. No. 07/355,008, filed May 18 1989; and U.S. Ser. No. 7/456,637, the disclosures of which are incorporated herein by reference. "HCV" as used herein includes the pathogenic strains capable of causing hepatitis C, and attenuated strains or defective interfering particles derived therefrom. The HCV genome is comprised of RNA. It is known that RNA-containing viruses have relatively high rates of spontaneous mutation, reportedly on the order of $10^{-3}$ to $10^{-4}$ per incorporated nucleotide (Fields & Knipe, "Fundamental Virology" (1986, Raven Press, N.Y.)). As heterogeneity and fluidity of genotype are inherent characteristics of RNA viruses, there will be multiple strains/isolates, which may be virulent or avirulent, within the HCV species.

Information on several different strains/isolates of HCV is disclosed herein, particularly strain or isolate CDC/HCVI (also called HCV1). Information from one strain or isolate, such as a partial genomic sequence, is sufficient to allow those skilled in the art using standard techniques to isolate new strains/isolates and to identify whether such new strains/isolates are HCV. Typically, different strains, which may be obtained from a number of human sera (and from different geographical areas), are isolated utilizing the information from the genomic sequence of HCV1.

HCV is now classified as a new genus of the Flavinidae family of which the other two genera are pestivirus and flavivirus. The Flavivirus family contains a large number of viruses which are small, enveloped pathogens of man. The morphology and composition of Flavivirus particles are known, and are discussed in M. A. Brinton, in "The Viruses: The Togaviridae And Flaviviridae" (Series eds. Fraenkel-Conrat and Wagner, vol. eds. Schlesinger and Schlesinger, Plenum Press, 1986), pp. 327–374. Generally, with respect to morphology, Flaviviruses contain a central nucleocapsid surrounded by a lipid bilayer. Virions are spherical and have a diameter of about 40–50 nm. Their cores are about 25–30 mn in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HCV and encode a polyprotein precursor of about 3500 amino acids. Individual viral proteins are cleaved from this precursor polypeptide.

The genome of HCV appears to be single-stranded RNA containing about 10,000 nucleotides. The genome is positive-stranded, and possesses a continuous translational open reading frame (ORF) that encodes a polyprotein of about 3,000 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the non-structural proteins of the Flavivirus family, and with the pestiviruses (which are now also considered to be part of the Flavivirus family).

The HCV polyprotein is processed by the host and viral proteases during or after translation. The genetic map of HCV is as follows: from the amino terminus to the carboxy terminus, the nucleocapsid protein (C), the envelope proteins (E1) and (E2), and the non-structural proteins 2, 3, 4 (a+b), and 5 (a+b) (NS2, NS3, NS4, and NS5). Based upon the putative amino acids encoded in the nucleotide sequence of HCV1, a small domain at the extreme N-terminus of the HCV polyprotein appears similar both in size and high content of basic residues to the nucleocapsid protein (C) found at the N-terminus of flaviviral polyproteins. The non-structural proteins 2,3,4, and 5 (NS2–5) of HCV and of yellow fever virus (YFV) appear to have counterparts of similar size and hydropathicity, although the amino acid sequences diverge. However, the region of HCV which would correspond to the regions of YFV polyprotein which contains the M, E, and NS1 protein not only differs in sequence, but also appears to be quite different in size and hydropathicity. Thus, while certain domains of the HCV genome may be referred to herein as, for example, E1, E2, or NS2, it should be understood that these designations are for convenience of reference only; there may be considerable differences between the HCV family and flaviviruses that have yet to be appreciated and as these differences surface, domain designations may change.

Due to the evolutionary relationship of the strains or isolates of HCV, putative HCV strains and isolates are identifiable by their homology at the polypeptide level. With respect to the isolates disclosed herein, new HCV strains or isolates are expected to be at least about 40% homologous, some more than about 70% homologous, and some even more than about 80% homologous: some may be more than about 90% homologous at the polypeptide level. The techliques for determining amino acid sequence homology are known in the art. For example, the amino acid sequence may be determined directly and compared to the sequences provided herein. Alternatively the nucleotide sequence of the genomic material of the putative HCV may be determined (usually via a cDNA intprmediate), the amino acid sequence encoded therein can be determined, and the corresponding regions compared.

The term "NS3 protein fragment showing helicase activity" or "NS3 protein helicase fragment" refers to an enzyme derived from an HCV NS3 protein which exhibits helicase activity, specifically the portion of polypeptide that is encoded in the carboxy two-third terminus of the NS3 domain of the HCV genome. Generally, the portion of the HCV NS3 protein showing protease activity, i.e., that is found in the amino one-third terminus has been removed. At least one strain of HCV contains a NS3 protein fragment showing helicase activity believed to be substantially encoded by or within the following sequence of amino acids residues within the NS3 protein fragment i.e.; approximately amino acids 1193 to 1657 of the NS3 protein shown in FIG. 1. The sequence of such helicase is depicted below:

1193  Val Asp Phe Ile Pro Val Glu Asn Leu Glu  (SEQ ID NO: 2)
      Thr Thr Met Arg Ser Pro Val Phe Thr Asp
      Asn Ser Ser Pro Pro Val Val Pro Gln Ser
      Phe Gln Val Ala His Leu His Ala Pro Thr
      Gly Ser Gly Lys Ser Thr Lys Val Pro Ala
      Ala Tyr Ala Ala Gln Glu Tyr Lys Val Leu
      Val Leu Asn Pro Ser Val Ala Ala Thr Leu
      Gly Phe Gly Ala Tyr Met Ser Lys Ala His
                      (Leu)
      Gly Ile Asp Pro Asn Ile Arg Thr Gly Val
      Arg Thr Ile Thr Thr Gly Ser Pro Ile Thr
      Tyr Ser Thr Tyr Gly Lys Phe Leu Ala Asp
      Gly Gly Cys Ser Gly Gly Ala Tyr Asp Ile
      Ile Ile Cys Asp Glu Cys His Ser Thr Asp
      Ala Thr Ser Ile Leu Gly Ile Gly Thr Val
      Leu Asp Gln Ala Glu Thr Ala Gly Ala Arg
      Leu Val Val Leu Ala Thr Ala Thr Pro Pro
      Gly Ser Val Thr Val Pro His Pro Asn Ile
      Glu Glu Val Ala Leu Ser Thr Thr Gly Glu
      Ile Pro Phe Tyr Gly Lys Ala Ile Pro Leu
      Glu Val Ile Lys Gly Gly Arg His Leu Ile
      Phe Cys His Ser Lys Lys Lys Cys Asp Glu
      Leu Ala Ala Lys Leu Val Ala Leu Gly Ile
      Asn Ala Val Ala Tyr Tyr Arg Gly Leu Asp
      Val Ser Val Ile Pro Thr Ser Gly Asp Val
      Val Val Val Ala Thr Asp Ala Leu Met Thr
      Gly Tyr Thr Gly Asp Phe Asp Ser Val Ile
          (Tyr)
      Asp Cys Asn Thr Cys Val Thr Gln Thr Val
                      (Ser)
      Asp Phe Ser Leu Asp Pro Thr Phe Thr Ile
      Glu Thr Ile Thr Leu Pro Gln Asp Ala Val
      Ser Arg Thr Gln Arg Arg Gly Arg Thr Gly
      Arg Gly Lys Pro Gly Ile Tyr Arg Phe Val
      Ala Pro Gly Glu Arg Pro Ser Gly Met Phe
      Asp Ser Ser Val Leu Cys Glu Cys Tyr Asp
      Ala Gly Cys Ala Trp Tyr Glu Leu Thr Pro
      Ala Glu Thr Thr Val Arg Leu Arg Ala Tyr
      Met Asn Thr Pro Gly Leu Pro Val Cys Gln
      Asp His Leu Glu Phe Trp Glu Gly Val Phe
      Thr Gly Leu Thr His Ile Asp Ala His Phe

```
            -continued
Leu Ser Gln Thr Lys Gln Ser Gly Glu Asn

Leu Pro Tyr Leu Val Ala Tyr Gln Ala Thr

Val Cys Ala Arg Ala Gln Ala Pro Pro Pro

Ser Trp Asp Gln Met Trp Lys Cys Leu Ile

Arg Leu Lys Pro Thr Leu His Gly Pro Thr

Pro Leu Leu Tyr Arg Leu Gly Ala Val Gln

Asn Glu Ile Thr Leu Thr His Pro Val Thr

Lys Tyr Ile Met Thr Cys Met Ser Ala Asp

Leu Glu Val Val Thr                    1657
```

The above N and C termini of the helicase fragment are putative, the actual termini being defined by expressing and processing in an appropriate host of a DNA construct encoding the entire NS3 domain. It is understood that this sequence may vary from strain to strain, as RNA viruses, like HCV, are known to exhibit a great deal of variation. Further, the actual N and C termini may vary, as the NS3 protein fragment showing helicase activity is cleaved from a precursor polyprotein: variations in the helicase amino acid sequence can result in different termini for helicase activity. Thus, the amino- and carboxy-termini may differ from strain to strain of HCV. A minimum sequence necessary for activity does exist and has been determined herein. The sequence of the NS3 fragment may be truncated at either end by treating an appropriate expression vector with exonuclease after cleavage with a restriction endonuclease at the 5' or 3' end of the coding sequence to remove any desired number of base pairs. The resulting coding polynucleotide is then expressed and the sequence determined. In this manner the activity of the resulting product may be correlated with the amino acid sequence: a limited series of such experiments (removing progressively greater numbers of base pairs) determines the minimum internal sequence necessary for helicase activity. The sequence of the HCV NS3 fragment may be substantially truncated, particularly at the carboxy terminus up to approximately 50 amino acids, with full retention of helicase activity. Successive carboxy truncations do eventually result in the loss of helicase activity. Further carboxy truncation, at around 135 amino acids results in the loss of NTPase activity. The amino terminus of the NS3 fragment, i.e., that beginning around 1190 of the HCV-1 amino acid sequence may also be truncated to a degree without a loss of helicase activity. Surprisingly, an amino terminus truncation to around twenty amino acids of the putative helicase domain does, however, result in an increase in the solubility of the fragment in purification and assay buffers. The NS3 protein generally is insoluble in buffers. When approximately 20 amino acids of helicase N terminus are deleted, the fragments become soluble in buffer. When approximately thirty-five amino acids are deleted, however, the fragments lose both NTPase and helicase activity. It is known that a portion of the NS3 protein at the amino terminus i.e., that beginning around amino acid 1027 exhibits protease activity. Protease activity, however, is not required of the HCV helicases of the invention and, in fact, the amino terminus fragments of NS3 exhibiting protease activity have been deleted from the helicase or fragments of the present invention.

"HCV NS3 fragment helicase analogs" refer to polypeptides which vary from the NS3 carboxy fragment having helicase activity, shown above, by deletion, alteration and/or addition to the amino acid sequence of the native helicase fragment. HCV NS3 helicase fragment analogs include the truncated helicase fragments described above, as well as HCV NS3 fragment helicase mutants and fusion helicase fragments comprising HCV NS3 protein helicase fragments, truncated NS3 protein helicase fragments, or NS3 fragment helicase mutants. Alterations to form HCV NS3 fragment helicase mutants are preferably conservative amino acid substitutions, in which an amino acid is replaced with another naturally-occurring amino acid of similar character. For example, the following substitutions are considered "conservative":

Gly↔Ala; Asp↔Glu; Val↔Ile↔Leu;

Lys↔Arg; Asn↔Gln; and Phe↔Trp↔Tyr.

Nonconservative changes are generally substitutions of one of the above amino acids with an amino acid from a different group (e.g., substituting Asn for Glu), or substituting Cys, Met, His, or Pro for any of the above amino acids. Substitutions involving common amino acids are conveniently performed by site specific mutagenesis of an expression vector encoding the desired protein, and subsequent expression of the altered form. One may also alter amino acids by synthetic or semi-synthetic methods. For example, one may convert cysteine or serine residues to selenocysteine by appropriate chemical treatment of the isolated protein. Alternatively, one may incorporate uncommon amino acids in standard in vitro protein synthetic methods. Typically, the total number of residues changed, deleted or added to the native sequence in the mutants will be no more than about 20, preferably no more than about 10, and most preferably no more than about 5.

The term fusion protein generally refers to a polypeptide comprising an amino acid sequence drawn from two or more individual proteins. In the present invention, "fusion protein" is used to denote a polypeptide comprising the HCV NS3 helicase fragment, truncate, mutant or a functional portion thereof, fused to a non-HCV protein or polypeptide ("fusion partner"). Fusion proteins are most conveniently produced by expressing of a fused gene, which encodes a portion of one polypeptide at the 5' end and a portion of a different polypepitide at the 3' end, where the different portions are joined in one reading frame which may be expressed in a suitable host. It is presently preferred (although not required) to position the HCV NS3 helicase fragment or analog at the carboxy terminus of the fusion protein, and to employ a functional enzyme fragment at the amino terminus. The HCV NS3 helicase fragment is normally expressed within a large polyprotein. The helicase fragment is not expected to include cell tnansport signals (e.g., export or secretion signals). Suitable functional enzyme fragments are those polypeptides which exhibit a quantifiable activity when expressed fused to the HCV NS3 helicase fragment. Exemplary enzymes include, without limitation, β-galactosidase (β-gal), β-lactamase, horseradish peroxidase (HRP), glucose oxidase (GO), human superoxide dismutase (hSOD), urease, and the like. These enzymes are convenient because the amount of fusion protein produced can be quantified by means of simple colorimetric assays. Alternatively, one may employ fragments or antigenic proteins, to permit simple detection by metal-binding columns and quantification of fusion proteins using antibodies specific for the fusion partner. The presently preferred fusion partner is six histidine residues at the carboxy terminus.

B. General Method

The practice of the present invention generally employs conventional techniques of molecular biology, microbiology, recombinant DNA, and immunology, which are within the skill of the art. Such techniques are explained fully in the literature. See for example J. Sambrook et al, "Molecular Cloning; A Laboratory Manual (1989); "DNA Cloning", Vol. I and II (D. N Glover ed. 1985); "Oligonucleotide Synthesis" (M. J. Gait ed, 1984); "Nucleic Acid Hybridization" (B. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods In Enzymology" (Academic Press, Inc.); "Gene Transfer Vectors For Mammalian Cells" (J. H. Miller and M. P. Calos eds. 1987, Cold Spring Harbor Laboratory); *Meth Enzymol* (1987) 154 and 155 (Wu and Grossman, and Wu, eds., respectively); Mayer & Walker, eds. (1987), "Immunochemical Methods In Cell And Molecular Biology" (Academic Press, London); Scopes, "Protein Purification: Principles And Practice", 2nd Ed (Springer-Verlag, N.Y., 1987); and "Handbook Of Experimental Immunology", volumes I–IV (Weir and Blackwell, eds, 1986).

Both prokaryotic and eukaryotic host cells are useful for expressing desired coding sequences when appropriate control sequences compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These plasmids are commercially available. The markers may be used to obtain successful transformants by selection. Commonly used prokaryotic control sequences include the T7 bacteriophage promoter (Dunn and Studier, *J. Mol. Biol.* (1983) 166:477) the β-lactamase (penicilliase) and lactose promoter systems (Chang et al, *Nature* (1977) 198:1056), the tryptophan (trp) promoter system (Goeddel et al, *Nuc Acids Res* (1980) 8:4057) and the lambda-derived P$_L$ promoter and N gene ribosome binding site (Shimatake et al, *Nature* (1981) 292:128) and the hybrid tac promoter (De Boer et al, *Proc Nat Acad Sci USA* (1983) 292:128) derived from sequences of the trp and lac UV5 promoters. The foregoing systems are particularly compatible with *E. coli*; if desired, other prokaryotic hosts such as strains of Bacillus or Pseudomonas may be used, with corresponding control sequences.

Eukaryotic hosts include, without limitation, yeast and mammalian cells in culture systems. Yeast expression hosts include Saccharomnyces, Klebsiella, Picia, and the like. *Saccharomyces cerevisiae* and *Saccharomyces carlsbergensis* and *K. lactis* are the most commonly used yeast hosts, and are convenient fungal hosts. Yeast-compatible vectors carry markers which permit selection of successful transformants by conferring prototrophy to auxotrophic mutants or resistance to heavy metals on wild-type strains. Yeast compatible vectors may employ the 2μ origin of replication (Broach et al, *Meth Enzymol* (1983) 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al, *J Adv Enzyme Reg* (1968) 7:149; Holland et al, *Biochem* (1978), 17:4900), including the promoter for 3-phosphoglycerate kinase (R. Hitzeman et al, *J Biol Chem* (1980) 255:2073). Terminators may also be included, such as those derived from the enolase gene (Holland, *J Biol Chem* (1981) 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, a leader sequence derived from yeast α-factor (see U.S. Pat. No. 4,870,008, incorporated herein by reference).

A presently preferred expression system employs the ubiquitin leader as the fusion partner. Copending application U.S. Ser. No. 7/390,599 filed Aug. 7, 1989 disclosed vectors for high expression of yeast ubiquitin fusion proteins. Yeast ubiquitin provides a 76 amino acid polypeptide which is automatically cleaved from the fused protein upon expression. The ubiquitin amino acid sequence is as follows:

(SEQ ID NO:3)

Gln Ile Phe Val Lys Thr Leu Thr Gly Lys

Thr Ile Thr Leu Glu Val Glu Ser Ser Asp

Thr Ile Asp Asn Val Lys Ser Lys Ile Gln

Asp Lys Glu Gly Ile Pro Pro Asp Gln Gln

Arg Leu Ile Phe Ala Gly Lys Gln Leu Glu

Asp Gly Arg Thr Leu Ser Asp Tyr Asn Ile

Gln Lys Glu Ser Thr Leu His Leu Val Leu

Arg Leu Arg Gly Gly

See also Ozkaynak et al, *Nature* (1984) 312:663–66. Polynucleotides encoding the ubiquitin polypeptide may be synthesized by standard methods, for example following the technique of Barr et al, *J Biol Chem* (1988) 268:1671–78 using an Applied Biosystem 380A DNA synthesizer. Using appropriate linkers, the ubiquitin gene may be inserted into a suitable vector and ligated to a sequence encoding the HCV helicase or a fragment thereof.

In addition, the transcriptional regulatory region and the transcriptional initiation region which are operably linked may be such that they are not naturally associated in the wild-type organism. These systems are described in detail in EPO 120,551, published Oct. 3, 1984; EPO 116,201, published Aug. 22, 1984; and EPO 164,556, published Dec. 18, 1985, all of which are commonly owned with the present invention, and are hereby incorporated herein by reference in full.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers et al, *Nature* (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art.

Vectors suitable for replication in mammalian cells are known in the art, and may include viral replicons, or sequences which insure integration of the appropriate sequences encoding HCV epitopes into the host genome. For example, another vector used to express foreign DNA is Vaccinia virus. In this case the heterologous DNA is inserted into the Vaccinia genome. Techniques for the insertion of foreign DNA into the vaccinia virus genome are known in the art, and may utilize, for example, homologous recombination. The heterologous DNA is generally inserted into a gene which is nonessential to the virus, for example, the thymidine kinase gene (tk), which also provides a selectable marker. Plasmid vectors that greatly facilitate the construction of recombinant viruses have been described (see, for example, Mackett et al, *J Virol* (1984) 49:857; Chakrabarti et al, *Mol Cell Biol* (1985) 5:3403; Moss, in GENE TRANSFER VECTORS FOR MAMMALIAN CELLS (Miller and Calos, eds., Cold Spring Harbor Laboratory, NY, 1987), p. 10). Expression of the HCV polypeptide then occurs in cells or animals which are infected with the live recombinant vaccinia virus.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373 (see PCT WO89/046699 and U.S. Ser. No. 7/456,637). Many other vectors known to those of skill in the art have also been designed for improved expression. These include, for example, pVL985 (which alters the polyhedrin start codon from ATG to ATT, and introduces a BamHI cloning site 32 bp downstream from the ATT; See Luckow and Summers, *Virol* (1989) 17:31). AcNPV transfer vectors for high level expression of nonfused foreign proteins are described in copending applications PCT WO89/046699 and U.S. Ser. No. 7/456,637. A unique BamHI site is located following position-8 with respect to the translation initiation codon ATG of the polyhedrin gene. There are no cleavage sites for SmaI, PstI, BglII, XbaI or SstI. Good expression of nonfused foreign proteins usually requires foreign genes that ideally have a short leader sequence containing suitable translation initiation signals preceding an ATG start signal. The plasmid also contains the polyhedrin polyadenylation signal and the ampicillin-resistance (amp) gene and origin of replication for selection and propagation in *E. coli*.

Methods for the introduction of heterologous DNA into the desired site in the baculovirus virus are known in the art. (See Summer and Smith, Texas Agricultural Experiment Station Bulletin No. 1555; Smith et al, *Mol Cell Biol* (1983) 3:2156–2165; and Luckow and Summers, *Virol* (1989) 17:31). For example, the heterologous DNA can be inserted into a gene such as the polyhedrin gene by homologous recombination, or into a restriction enzyme site engineered into the desired baculovirus gene. The inserted sequences may be those that encode all or varying segments of the polyprotein, or other orfs that encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for post-translational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($IL2_s$) which signals for secretion from the cell, is recognized and properly removed in insect cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen, *Proc Nat Acad Sci USA* (1972) 69:2110; T. Maniatis et al, "Molecular Cloning; A Laboratory Manual" (Cold Spring Harbor Press, Cold Spring Harbor, N.Y., 1982). Yeast transformation by direct uptake may be carried out using the method of Hinnen et al, *Proc Nat Acad Sci USA* (1978) 75:1929. Mammalian transformations by direct uptake may be conducted using the calcium phosphate precipitation method of Graham and Van der Eb, *Virol* (1978) 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

Vector construction employs techniques which are known in the art. Site-specific DNA cleavage is performed by treating with suitable restriction enzymes under conditions which generally are specified by the manufacturer of these commercially available enzymes. In general, about 1 $\mu$g of plasmid or DNA sequence is cleaved by 1 unit of enzyme in about 20 $\mu$L buffer solution by incubation for 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures described in *Meth Enzymol* (1980) 65:499–560.

Sticky-ended cleavage fragments may be blunt ended using *E. coli* DNA polymerase I (Klenow fragment) with the appropriate deoxynucleotide triphosphates (dNTPs) present in the mixture. Treatment with S1 nuclease may also be used, resulting in the hydrolysis of any single stranded DNA portions.

Ligations are carried out under standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate, thus preventing religation of the vector. Alternatively, restriction enzyme digestion of unwanted fragments can be used to prevent ligation.

Ligation mixtures are transformed into suitable cloning hosts, such as *E. coli*, and successful transformants selected using the markers incorporated (e.g., antibiotic resistance), and screened for the correct construction.

Synthetic oligonucleotides may be prepared using an automated oligonucleotide synthesizer as described by Warner, *DNA* (1984) 3:401. If desired, the synthetic strands may be labeled with $^{32}P$ by treatment with polynucleotide kinase in the presence of $^{32}P$-ATP under standard reaction conditions.

DNA sequences, including those isolated from cDNA libraries, may be modified by known techniques, for example by site directed mutagenesis (see e.g., Zoller, *Nuc Acids Res* (1982) 10:6487). Briefly, the DNA to be modified is packaged into phage as a single stranded sequence, and converted to a double stranded DNA with DNA polymerase, using as a primer a synthetic oligonucleotide complementary to the portion of the DNA to be modified, where the desired modification is included in the primer sequence. The resulting double stranded DNA is transformed into a phage-supporting host bacterium. Cultures of the transformed bacteria which contain copies of each strand of the phage are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

DNA libraries may be probed using the procedure of Grunstein and Hogness *Proc Nat Acad Sci USA* (1975) 73:3961. Briefly, in this procedure the DNA to be probed is immobilized on nitrocellulose filters, denatured, and prehybridized with a buffer containing 0–50% formamide, 0.75 M NaCl, 75 mM Na citrate, 0.02% (wt/v) each of bovine serum albumin, polyvinylpyrrolidone, and Ficoll®, 50 mM $NaH_2PO_4$ (pH 6.5), 0.1% SDS, and 100 µg/mL carrier denatured DNA. The percentage of formamide in the buffer, as well as the time and temperature conditions of the prehybridization and subsequent hybridization steps depend on the stringency required. Oligomeric probes which require lower stringency conditions are generally used with low percentages of formamide, lower temperatures, and longer hybridization times. Probes containing more than 30 or 40 nucleotides, such as those derived from cDNA or genomic sequences generally employ higher temperatures, e.g., about 40–42° C., and a high percentage formamide, e.g., 50%. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

For routine vector constructions, ligation mixtures are transformed into *E. coli* strain HB101 or other suitable hosts, and successful transformnants selected by antibiotic resistance or other markers. Plasmids from the transformants are then prepared according to the method of Clewell et al, *Proc Nat Acad Sci USA* (1969) 62:1159, usually following chloramphenicol amplification (Clewell, *J Bacteriol* (1972) 110:667). The DNA is isolated and analyzed, usually by restriction enzyme analysis and/or sequencing. Sequencing may be performed by the dideoxy method of Sanger et al, *Proc Nat Acad Sci USA* (1977) 74:5463, as further described by Messing et al, *Nuc Acids Res* (1981) 9:309, or by the method of Maxam et al, *Meth Enzymol* (1980) 65:499. Problems with band compression, which are sometimes observed in GC-rich regions, were overcome by use of T-deazoguanosine according to Barr et al, *Biotechniques* (1986) 4:428.

The enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microtiter dish, plastic cup, dipstick, plastic bead, or the like), incubated with test serum dilutions, washed, incubated with anti-immunoglobulin labeled with an enzyme, and washed again. Enzymes suitable for labeling are known in the art, and include, for example, horseradish peroxidase (HRP). Enzyme activity bound to the solid phase is usually measured by adding a specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is measured colorimetrically, and related to antigen concentration.

The NS3 proteins of the three genera of Flavivitidea: flavivirus, pestivirus and HCV, have conserved sequence motifs of serine type proteinase and of nucleoside triphosphatase (NTPase)/RNA helicase. See FIG. 2. The NTPase/RNA helicase carboxy two-thirds of the NS3 protein fragment belongs to the DEAD box family. The DEAD box protein family has eight highly consenred amino acid motifs, one of which is the DEAD region where it is also known as an ATPase motif. The DEAD protein family consists of three subfamilies: DEAD proteins, DEAH proteins and DEXH proteins. FIG. 3 shows the conserved sequence motifs of DEXH protein family and the corresponding motifs of HCV NS3. The HCV NS3 protein has sequence motif of DECH which results in its classification in the DEXH protein subfamily.

The HCV NS3 protein fragments disclosed herein have similar characteristics with other known RNA helicases, i.e., they show RNA helicase activity only in the presence of divalent cations ($Mn^{2+}$ or $Mg^{2+}$) and ATP. At a lower level of ATP, (approximately 1 mM) an increasing amount of either cation inhibits the enzymatic activity of the NS3 fragment. When the ATP concentration is high, (approximately 5 mM), helicase activity remains at a high level even when $Mg^{2+}$ or $Mn^{2+}$ cations are present at high concentrations. RNA helicase A purified from HeLa cells, needs only $Mg^{2+}$ for its cofactor, and $Mn^{2+}$ does not substituted for $Mg^{2+}$. See Lee et al., *J. Biol.* 267:4398–4407 (1992), incorporated herein by reference. Pestivirus NS3 and Vaccinia virus RNA helicase have shown to use both cations. Likewise, HCV NS3 protein helicase fragments disclosed herein can utilize both metal ions.

The helicase activity of the HCV NS3 protein helicase fragments is likely pH specific. The experiments in the examples were carried out at pH 6.5. When the pH was increased to 7.6, however, HCV NS3 protein helicase fragments showed not more than 10% strand separation, keeping all other components constant. (data not shown) These characteristics of HCV NS3 protein helicase fragments imply that it has a similar nature to pestivirus NS3 RNA helicase, which is known to pH sensitive.

RNA helicase activity was confirmed not to be derived from *E. coli* contaminants in two ways. First, a pET21b plasmid without a HCV NS3 protein fragment insert was used as a negative control. The enzymatic activity of the same eluted fraction from the negative control cell culture was tested and there was no detectable level of NTPase or RNA helicase activity. Second, the NS3 protein fragment's helicase activity was inhibited by a NS3-specific monoclonal antibody, but, an unrelated antibody did not affect the activity. From these results, it was determined that the helicase activity was derived not from *E. coli* contaminants, but from the HCV NS3 protein fragments.

Most of the investigated RNA helicases bound to single strand region and then unwound double strand RNA by moving unidirectionaly or bidirectionaly. The substrate with the single strand region on both 3' and 5' ends was used. Suzich et al., *J. Virol.*, 67:6152–6158 (1993) showed that the two thirds of the C'-terminal of HCV NS3 could hydrolyze all NTPs and dNTPs. This NTPase activity was observed with the HCV NS3 protein fragments disclosed herein. (data not shown) The results showing that the truncated NS3 protein fragments described herein having biochemical helicase activity in spite of deleted N'-terminal proteinase domain suggest that the proteinase and NTPase domains may act independently.

The HCV NS3 protein fragments showing helicase activity of the present invention are advantageous because they are soluble in purification and assay buffers, while the entire NS3 protein generally is not. The solubility of the helicase fragments was determined by first constructing several clones from various vectors and fusion proteins. For example, a pGEX-2T vector containing a glutathione-s-transferase (GST) fusion protein was used to clone the HCV NS3 protein i.e., from 1027 to 1657 a.a. of HCV-1. The resulting fusion protein of GST and HCV NS3 protein was insoluble, i.e., the only portion of the fusion protein that was isolated was that from the insoluble portion of the bacterial extract. That fusion protein was solubilized by denaturing with 6 M urea. When the denatured fusion protein was refolded by serial dialysis against a concentration step gradient, only a small fraction of the renatured fusion protein was correctly refolded and no enzymatic activity was observed in the renatured protein. When an HCV NS3 protein was fused with a maltose binding protein using a pMAL vector, the fusion protein was soluble. The molecular weight of the fusion protein, however, was relatively large (M.W. 110 kDa) because the maltose binding protein itself is about 40 kDa. Thus, such a fusion protein is undesirable to use. In addition, it is difficult to separate the maltose binding protein domain out from the fusion protein containing it and the HCV NS3 protein. In addition, a pET21b vector was utilized to express the domain of HCV NS3 protein, amino acids 1027 to 1657. The expression level of the protein was very low and only a small quantity of the protein was isolated.

Thus, the HCV NS3 protein fragments of the present invention in, e.g., a pET vector system, provides the following advantages:

1) a better T7 promoter system when compared to the promoters of pMAL or pGEX vector;
2) an increase in solubility of the expressed NS3 protein fragment having helicase activity;
3) an elimination of the necessity to remove the non-HCV NS3 protein fragment from the fusion protein; and
4) a convenient purification step by using nickel column chromatography.

Further, a soluble NS3 protein fragment having helicase activity has several advantages to the insoluble full lentgth protein. First, it is not necessary for the soluble protein fragments to denature and refold for use in purification and enzyme assays. An insoluble protein or fragment needs to be denatured by urea or Guanidium-HC1 for purification and then must be dialyzed against a concentration step gradient for removing the urea or Guanidium-HC1 before refolding and recovery of the enzymatic activity of the protein fragment. Second, the yield of soluble NS3 protein fragments from expression systems is higher than that of insoluble NS3 protein fragments. During the denaturation-refolding process, an insoluble protein fragment is lost in a large portion of the cell extract. Third, the enzymatic activity of the insoluble NS3 proteins cannot be observed after refolding.

Soluble helicase fragments of a HCV NS3 protein can be used to screen for specific helicase inhibitors from a combinatorial library. The screening assay can be performed based on the mobility shift of the double stranded template RNA in a polyacrylamide gel by studying the unwinding activity of the helicase fragment. The screening assay can also be automated in a microtiter dish (96-well plate) format. In the latter assay, the double-stranded template RNA is labeled with biotin at the 5'-end of one strand and with $^{32}P$ at the 5'-end of the other strand. This labeled template can be attached to the bottom of the well that is coated with streptoavidin. The helicase activity from the added fragments can be measured by counting radioactivity from the displaced $^{32}P$-labeled RNA strand that is now present in the well supernatant. Potential helicase inhibitors present in the combinatorial library can be found by detecting specific inhibition of the strand displacement reaction by helicase fragments.

C. Examples

The examples presented below are provided as a further guide to the practitioner of ordinary skill in the art, and are not to be construed as limiting the invention in any way.

EXAMPLE 1

Expression and Purification of HCV NS3 Protein.

For expressing the carboxy two-thirds of HCV NS3 protein, the polymerase chain reaction (PCR) was used to amplify a 1.4 Kb DNA fragment encompassing amino acids 1193 to 1657 from HCV-1 cDNA. The sense primer used was JCK-1 5'-GGGGATCCGGTGGACTTTATCCCT-3' (SEQ ID NO: 4), and the antisense primer JCK-7 5'GGAAGCTTGCTGACGACCTCG-3' (SEQ ID NO: 5). The PCR produced was digested with BamHI and HindIII inserted into BamHI and HindIII sites of pET21b (purchased from Novagen. Wis.).[1] The recombinant plasmid was designated as pET21b-NS3HCV and transformed to *E. coli*

BL21 (DE3), and the inserted region was verified by sequencing. pET21b-NS3HCV consisted of 466 amino acid residues from the carboxy terminus of HCV NS3 and contained His-Tag (6 histidines) and 19 additional residues from the pET expression vector at C-terminal end for easier purification. About 54 kDa of (481 a.a residues) HCV NS3 His-tag fusion protein was induced by 1 mM IPTG from *E. coli* BL21 (DE3) harboring the recombinant plasmid to exponentially grow cells in LB medium with 10 μg/ml of ampicillin. (See FIG. 5, lanes 1 and 2).[2] From 200 ml of the culture, 400 μg of protein of approximately 95% purity was obtained. After 3 hrs of culturing at 37° C., the cells were harvested and disrupted. Soluble parts of cell extract were loaded onto a metal-binding column. Resin-bound protein was eluted with 1 M imidazole, 0.5 M NaCl, 20 mM Tris-Cl pH 7.9. Eluted fractions were subjected to SDS-PAGE, and protein-containing fractions were pooled and dialyzed against 50 mM Tris-Cl pH 7.9 for 4 hrs. The NTPase assay on polyetheleneimine cellulose TLC (J. T. Baker) was performed as previously described in Suzich et al., to confirm that final purified protein had active conformation. The purified protein showed an NTPase activity (data not shown).

Figure 6:
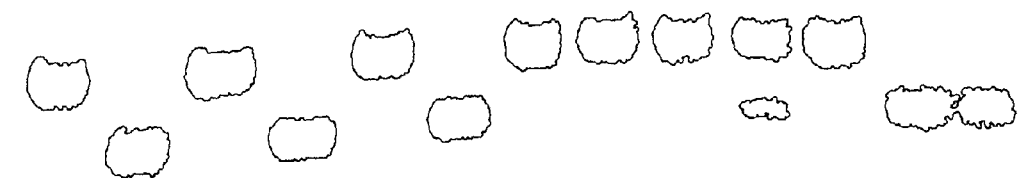
FIG. 6 shows the results of an RNA helicase assay of the HCV NS3 protein fragments. Lane 1; Fraction from negative control cell (pET vector only), Lane 2: 3 mM $Mn^{2+}$, Lane 3: no $Mn^{2+}$, Lane 4: 3 mM $Mg^{2+}$, Lane 5:no $Mg_{2+}$, Lane 6:3 mM KC1, Lane 7:no ATP, Lane 8:1 mM ATP, Lane 9:preincubation of the NS3 protein with NS3-specific monoclonal antibody, Lanes 10, 11: preincubation of the NS3 protein with anticonnexin monoclonal antibody at 0.5 μg, 1.0 μg per 20 μl, respectively. Monoclonal antibodies were preincubated with the S3 protein at room temperature for 5 min.

[1] As a negative control, a pET21b plasmid without the insert was transformed to *E. coli* BL21 (DE3) and induced with 1 mM IPTG. The negative control cell culture was processed with the same purification step as pET21b-NS3HCV. The negative control showed no enzymatic activity. See FIG. 6, lane 1.

[2] (One or more protein bands about 50 kDa appeared by IPTG induction, but only the 54 kDA NS3-His fusion protein was purified from the metal binding affinity column. (See FIG. 5, lane 3)

EXAMPLE 2
Preparation of Substrate for RNA Helicase.

FIG. 4 shows the structure of the double strand RNA used as a substrate of an RNA helicase. The long strand was prepared by in vitro transcription of pGEM1 that had been cleaved with PvuII, and the short strand was transcribed from the BamHI digested pSP65. Both strands were transcribed with SP6 RNA polymerase (New England Biolabs) according to the manufacturer's manual. After the transcription reaction, each aliquot was treated with RNase-free DNase (Promega) and extracted with phenol:chloroform, and precipitated with ethanol. Each RNA strand was resuspended with 25 μl of hybridization buffer (20 mM HEPES-KOH pH 7.6, 0.5 M NaCl, 1 mM EDTA, 0.1% SDS), and mixed. The mixture was heated to 100° C. for 5 min. and incubated at 65° C. for 30 min. and incubated at 25° C. overnight. The long strand RNA was labeled with [α-$^{32}$P]-CTP, and the specific activity of labeled substrated was 1–1.5×10$^5$ cpm/pmol ds RNA substrate.[3] Duplex RNA was electrophoresed on 6% native polyacrylamide gel (30:0.8), and the location of the ds RNA was identified by autoradiography. To recover the RNA substrate, a sliced gel fragment was ground in 400 μl of elution buffer (0.5 M annomium acetate, 0.1% SDS, 10 mM EDTA) and shaked vigorously at 4° C. for 2 hrs. The supernatants were extracted with chloroform and precipitated with ethanol, and the RNA pellet was dissolved in D.W.

[3] Strand displacement were observed by band shift of the radiolabeled long strand.

EXAMPLE 3
RNA Helicase Assay.

Figure 7A:
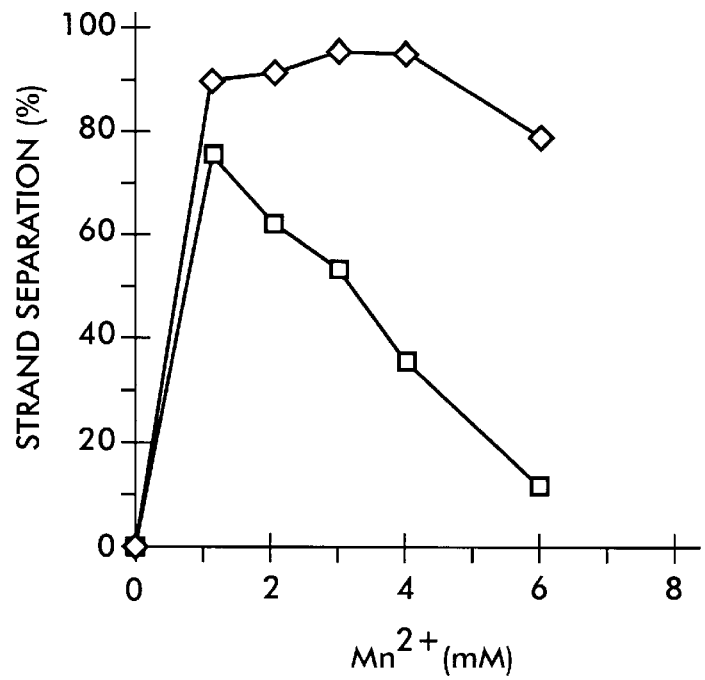
FIG. 7 shows the activity profiles of the HCV NS3 RNA fragment having helicase activity with different ATP and divalent cations concentrations. The effects of cations were tested at two different ATP concentrations (1 mM and 5 mM).
Figure 7B:
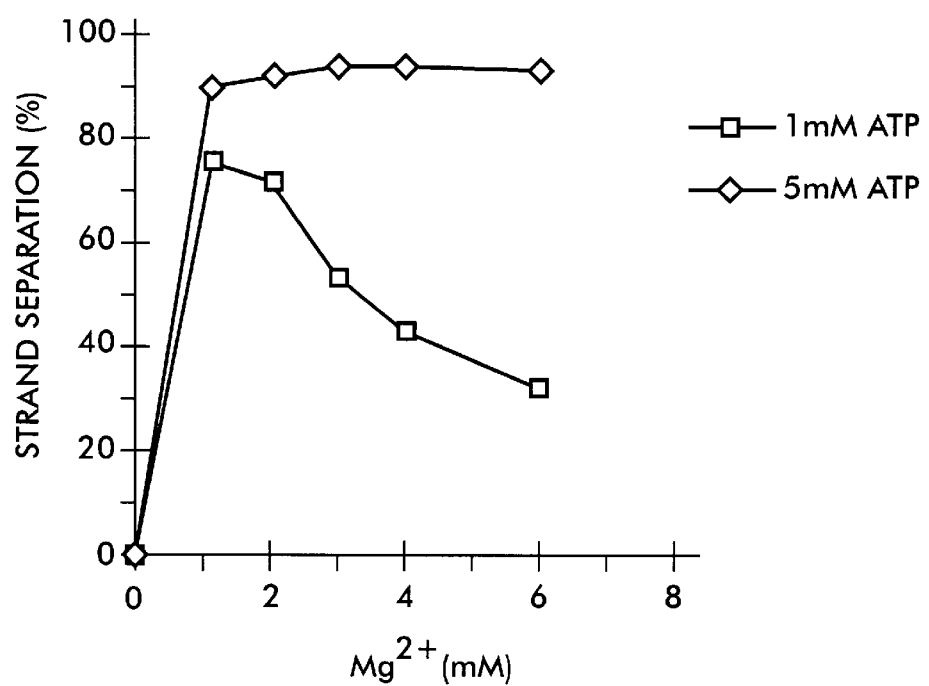

An RNA helicase assay was performed in 20 μl of reaction mixture: 1 pmol NS3 HCV protein fragment, 0.5 pmol ds RNA substrate, 25 mM MOPS-KOH (pH 6.5), 5 mM ATP, 3 mM MnCl$_2$, 2 mM DTT, 100 μg/ml BSA, and 2.5 U RNasin (Promega). The reaction mixture was incubated at 37° C. for 30 min. The reaction was stopped by adding 5 μl of 5× termination buffer [0.1 M Tris-Cl (pH 7.4), 20 mM EDTA, 0.5% SDS, 0.1% NP40, 0.1% bromophenol blue, 0.1% xylene cyanol, and 50% glycerol]. Each aliquot was loaded on 6% native polyacrylamide gel (30:0.8) and electrophoresed at 80 V for 3 hr. The ds RNA substrate and unwound RNA strand were visualized by autoradiography. The effect of ATP and divalent metal ion on the NS3 protein fragment's helicase activity was investigated by carrying out the same reactions with 1, 2, 3, 4, and 6 mM Mn$^{2+}$ or Mg$^{2+}$ in the presence of 1 mM or 5 mM ATP. Strand separation efficiencies were calculated by counting the radioactivities of the bands with PhosphoImager (Molecular Dynamics, Sunnyvale, Calif.). See FIG. 7 for the activity change of the HCV NS3 protein fragments at various concentrations of ATP and the divalent cations. The HCV NS3 RNA helicase fragments required divalent ions such as Mg$^{2+}$ and Mn$^{2+}$ (See FIG. 6, lane 2 to 5). Strand displacement was observed only when Mg$^{2+}$ or Mn$^{2+}$ ions were present (See FIG. 6, lanes 2 and 4). When either these divalent cations or ATP was deleted, ds RNA was not unwound (See FIG. 6, lanes 3, 5, and 7). Monovalent potassium ion did not activate the HCV NS3 protein fragment's helicase activity at these conditions (See FIG. 6, lane 6). At 1 mM ATP, the helicase activity was lower than at 5 mM (See FIG. 6, lane 8). Enzymatic activity of NS3 was inhibited by monoclonal antibodies of HCV NS3 protein fragments (See FIG. 6, lane 9), and was not blocked by a non-specific antibody at two different concentrations (See FIG. 6, lanes 10 and 11).

As mentioned above, RNA helicase activity of the HCV NS3 protein fragments was dependent on divalent cations and ATP. At low concentration of ATP (1 mM), helicase activity of NS3 was highest at a low concentration of either of the divalent cations, and, the helicase activity decreased when the concentration of the cations was increased. At high concentration of ATP (5 mM), most of the substrates were unwound at all of the tested cation concentrations. At 3 mM or 4 mM of cation concentration, either Mn$^{2+}$ or Mg$^{2+}$, the helicase activity was the highest. Thus, the helicase activity appears more sensitive to the divalent cation concentration in lower concentrations of ATP. In addition, the HCV NS3 protein fragments showed a slight bias for Mg$^{2+}$.

EXAMPLE 4
Testing of Truncated HCV NS3 Fragments for Helicase Activity

HCV NS3 fragments of varying sizes were expressed and purified as described above. The fragments were then tested for helicase activity as described above, and for NTPase activity as is known in the art. Table 1 depicts the fragments tested and whether the fragments showed helicase/NTPase activity. The following fragments were tested: No. 1, a full length helicase fragment, i.e., from amino acid 1193 to amino acid 1657 of the HCV NS3 domain, ATCC deposit no. 97306; No. 2, an HCV NS3 fragment having 10 amino acids deleted from the C-terminus of the HCV NS3 helicase domain, i.e., from amino acid 1193 to amino acid 1647 of the HCV NS3 domain, ATCC deposit no. 97307; No. 3, an HCV NS3 fragment having 30 amino acids deleted from the C-terminus of the HCV NS3 helicase domain, i.e., amino acid 1193 to amino acid 1627 of the HCV NS3 domain, ATCC deposit no. 97308; No. 4, an HCV NS3 fragment having 50 amino acids deleted from the C-terminus of the HCV NS3 helicase domain, i.e., amino acid 1193 to amino acid 1607 of the HCV NS3 domain, ATCC deposit no. 97309; No. 5, an HCV HS3 fragment having 97 amino acids deleted from the C-terminus of the HCV NS3 helicase domain, i.e., amino acid 1193 to amino acid 1560 of the HCV NS3 domain, ATCC deposit no. 97310; No. 6, an HCV NS3 fragment having 135 amino acids deleted from the C-terminus of the HCV NS3 helicase domain, i.e., amino acid 1193 to amino acid 1522 of the HCV NS3 domain, ATCC deposit no. 97311; No. 7, an HCV NS3 fragment having 16 amino acids deleted from the N-terminus of the HCV NS3 helicase domain, i.e., from amino acid 1209 to amino acid 1657 of the HCV NS3 domain, ATCC deposit no. 97312; and No. 8, an HCV NS3 fragment having 32 amino acids deleted from the N-terminus of the HCV NS3 helicase domain, i.e., from amino acid 1225 to amino acid 1657 of the HCV NS3 domain ATCC deposit no. 97313.

TABLE 1

| | NTPase | Helicase |
|---|---|---|
| 1. Full length | + | + |
| 2. C-10 a.a. | + | + |
| 3. C-30 a.a. | + | + |
| 4. C-50 a.a. | + | + |
| 5. C-97 a.a. | + | − |
| 6. C-135 a.a. | − | − |
| 7. N-16 a.a. | + | + |
| 8. N-32 a.a. | − | − |

As shown in Table 1, truncated mutants, numbers 5, 6, and 8 mutants did not demonstrate RNA helicase activity. Mutant 7, however, did demonstrate NTPase activity even though its activity was about half of No. 1 (full length) protein. Boiled RNA indicates denatured dsRNA after boiling for 5 min, and was therefore a control for ssRNA. As shown in Table 1, truncated fragments numbers 5, 6, and 8 lost RNA helicase activity.

EXAMPLE 5

Determining Solubility of the HCV NS3 Fragments

The solubility of the expressed protein from pET21b-HCVNS3 vector was determined by the following method: ITPG-induced cells were harvested at 6000 G for 5 mins. The cells were then resuspended with 1× binding buffer (5 mM imidazole, 500 mM NaCl, 20 mM Tris-Cl pH 7.9). The resuspended cells were then frozen in a dry ice-ethanol bath and thawed on ice and sonicated for 2 min. Cell extracts were centrifuged at 27000 G for 30 min. The soluble part of the cell extract, the supernatent and the insoluble part of the cell extract, the pellet, were subjected on SDS-PAGE. When a western blot was carried out for the SDS-PAGE using a monoclonal antibody against the HCV NS3 protein fragment, the expressed protein was observed only in the soluble part of the cell extract.

The above materials deposited with the ATCC under the accession numbers indicated, will be maintained under the terms of the Budapest Treaty on the International Recognition of the Deposit of Microorganisms for purposes of Patent Procedure. These deposits are provided as a convenience to those of skill in the art, and are not an admission that a deposit is required under 35 U.S.C. §112. The polynucleotide sequences contained in the deposited materials, as well as the amino acid sequence of the polypeptides encoded thereby, are incorporated herein by reference and are controlling in the event of any conflict with the sequences described herein. A license may be required to make, use or sell the deposited materials, and no such license is granted hereby.

What is claimed is:

1. A composition comprising a polynucleotide which encodes a truncated HCV NS3 fragment retaining helicase activity.

2. The composition of claim 1 wherein said truncated fragment retaining helicase activity is a truncation of SEQ ID NO:2.

3. A composition comprising a polynucleotide which encodes a fusion protein comprising a truncated HCV NS3 fragment retaining helicase activity and a fusion partner.

4. The composition of claim 3 wherein said fusion partner is selected from the group consisting of hSOD, yeast alpha-factor, IL-2S, ubiquitin, beta-galactoside, beta-lactamase, horseradish peroxidase, glucose oxidase, and urease.

5. The composition of claim 1 or 3 wherein said truncated fragment retaining helicase activity is a truncation of the sequence that spans from amino acid 1193 to amino acid 1657 in SEQ ID NO:6.

6. The composition of claim 5 wherein said fragment has its carboxy terminus at positions from amino acid 1561 to amino acid 1647.

7. The composition of claim 5 wherein said fragment has its amino terminus at positions from amino acid 1209 to amino acid 1223.

8. An expression vector for producing truncated HCV NS3 fragments retaining helicase activity in a host cell, which vector comprises:

a polynucleotide encoding a truncated HCV NS3 fragment retaining helicase activity;

transcriptional and translational regulatory sequences functional in said host cell operably linked to said fragment-encoding polynucleotide; and a selectable marker.

9. The vector of claim 8 further comprising a sequence encoding a fusion partner, linked to said fragment-encoding polynucleotide to form a fusion protein upon expression.

10. The vector of claim 9 wherein said fusion partner is selected from the group consisting of hSOD, yeast alpha-factor, IL-2S, ubiquitin, beta-galactoside, beta-lactamase, horseradish peroxidase, glucose oxidase, and urease.

11. The vector of claim 8 said truncated fragment retaining helicase activity is a truncation of the sequence that spans from amino acid 1193 to amino acid 1657 in SEQ ID NO:6.

12. The vector of claim 11 wherein said fragment has its carboxy terminus at positions from amino acid 1561 to amino acid 1647.

13. The vector of claim 11 wherein said fragment has its amino terminus at positions from amino acid 1209 to amino acid 1223.

14. A composition comprising a polynucleotide which encodes a truncated HCV NS3 fragment retaining helicase activity wherein said fragment has up to about 50 amino acids of the carboxy terminus deleted.

15. A composition comprising a polynucleotide which encodes a truncated HCV NS3 fragment retaining helicase activity wherein said fragment has up to about 20 amino acids of the amino terminus deleted.

* * * * *

UNITED STATES PATENT AND TRADEMARK OFFICE
CERTIFICATE OF CORRECTION

PATENT NO. : 5,989,905
DATED : November 23, 1999
INVENTOR(S) : Houghton et al.

It is certified that error appears in the above-identified patent and that said Letters Patent is hereby corrected as shown below:

<u>Title page,</u>
The order of inventors should appear as follows:

-- Jang Han, Michael Houghton, Qui-Lim Choo, Joonho Choe --.

Signed and Sealed this

Sixteenth Day of October, 2001

Attest:

*Nicholas P. Godici*

NICHOLAS P. GODICI
*Attesting Officer*     *Acting Director of the United States Patent and Trademark Office*